(12) United States Patent
Rosen et al.

(10) Patent No.: US 6,517,519 B1
(45) Date of Patent: Feb. 11, 2003

(54) DEVICE AND METHOD FOR RAPID CHEST TUBE INSERTION

(75) Inventors: Ron S. Rosen, McLean, VA (US); John C. Murphy, Clarksville, MD (US); Christopher Graham, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/637,386

(22) Filed: Aug. 11, 2000

Related U.S. Application Data

(60) Provisional application No. 60/148,937, filed on Aug. 13, 1999.

(51) Int. Cl.[7] .............................................. A61M 5/178
(52) U.S. Cl. ................... 604/164.06; 606/80; 606/167; 606/180
(58) Field of Search ...................... 604/164.01, 164.06, 604/264; 606/80, 167, 170, 180, 184, 185

(56) References Cited

U.S. PATENT DOCUMENTS

| | | | |
|---|---|---|---|
| 4,890,626 A | 1/1990 | Wang | 128/752 |
| 5,273,545 A | 12/1993 | Hunt et al. | 604/167 |
| 5,300,035 A * | 4/1994 | Clement | 604/167.01 |
| 5,312,363 A | 5/1994 | Ryan et al. | 604/167 |
| 5,324,270 A * | 6/1994 | Kayan et al. | 137/847 |
| 5,437,646 A * | 8/1995 | Hunt et al. | 137/849 |
| 5,478,329 A | 12/1995 | Ternamian | 604/274 |
| 5,591,191 A | 1/1997 | Kieturakis | 606/185 |
| 5,630,805 A | 5/1997 | Ternamian | 604/274 |
| 5,713,870 A * | 2/1998 | Yoon | 604/164.01 |
| 5,735,867 A * | 4/1998 | Golser et al. | 604/164.11 |
| 5,746,720 A | 5/1998 | Stouder, Jr. | 604/117 |
| 5,871,471 A | 2/1999 | Ryan et al. | 604/167 |
| 5,871,474 A | 2/1999 | Hermann et al. | 604/256 |
| 5,871,475 A | 2/1999 | Frassica | 604/264 |
| 5,882,344 A | 3/1999 | Stouder, Jr. | 604/264 |
| 5,895,377 A | 4/1999 | Smith et al. | 604/256 |
| 6,197,002 B1 * | 3/2001 | Peterson | 604/164.01 |

\* cited by examiner

Primary Examiner—William E. Tapolcai
(74) Attorney, Agent, or Firm—Benjamin Y. Roca

(57) ABSTRACT

The present invention is a device and method for gaining access, quickly and inexpensively, to a body cavity for the purpose of inserting into the cavity a medical device, such as a chest tube. The device generally comprises a catheter and a cannula insertable into the catheter during an insertion procedure. The cannula has a cutting tip that extends beyond one end of the catheter. The cutting tip enables simple insertion of the device into the body without requiring substantial pushing force. Once the device is inserted in the body, the cannula is removed, leaving a path of entry into the body cavity, while removing the sharp cutting tip from the area to reduce the likelihood of injury to a patient in whom the device is inserted.

7 Claims, 6 Drawing Sheets

DEVICE AND METHOD FOR RAPID CHEST TUBE INSERTION

CROSS-REFERENCE TO RELATED APPLICATIONS

This application is based on provisional U.S. application Ser. No. 60/148,937 filed on Aug. 13, 1999, incorporated fully herein by reference.

BACKGROUND OF THE INVENTION

1. Field of the Invention

The present invention relates to insertion devices used in medical procedures and methods of use of same.

2. Description of the Related Art

In the industrialized world, trauma is the leading cause of death in males under the age of forty. In the United States, chest injuries are responsible for one-fourth of all trauma deaths. Many of these fatalities could be prevented by early recognition of the injury followed by prompt management.

The lungs are surrounded by a pleural sac that consists of two membranes, the visceral and parietal pleurae. The parietal pleura lines the thoracic wall, and the visceral pleura surrounds the lung. The pleural space is a potential space between these two layers of pleurae. It contains a thin layer of serous pleural fluid that provides lubrication for the pleurae and allows the layers of pleurae to smoothly slide over each other during respiration.

Pneumothorax (air in the pleural space) and hemothorax (blood in the pleural space) are commonly occurring chest injuries. Pneumothorax and hemothorax are common consequences of chest trauma, second in frequency only to simple rib fractures, soft tissue injuries of the chest wall, and lung contusion. More importantly, pneumothorax and hemothorax are potentially lethal unless treated promptly. Common causes of pneumothorax and hemothorax include penetrating injuries (e.g., gunshot and stab wounds or injuries occurring as the result of a surgical procedure) and blunt injuries (e.g., from direct blows, crushing injuries, blasts, or falls). Pneumothorax may also occur as a result of the use of positive end-expiratory pressure (PEEP) in connection with mechanical ventilation procedures, or spontaneously as a result of emphysematous blebs (air spaces that may occur in the lung as a result of emphysema).

Normally, the pressure in the pleural space is much lower than the atmospheric pressure. Following trauma, air may enter the pleural space in several ways, e.g., through a communication between the pleural space and the outside air, or a leak from disrupted alveoli, bronchi or ruptured esophagus. The entry of air into the pleural space (pneuomthorax) results in an increase in the pressure in the pleural space. The increase of pressure in the pleural space compresses the lung, which can cause a potentially fatal condition known as a collapsed lung.

Eliminating pneumothorax requires prompt decompression of the pleural space, usually accomplished by the insertion of a chest tube and evacuation of the air. Similar procedures are followed during the occurrence of a hemothorax to remove blood from the pleural space. More specifically, in order to decompress the pleural cavity, a chest tube is inserted through the appropriate intercostal space, which is the area between adjacent ribs. Typically the intercostal space is approximately 1–2 cm in size. However, there are significant individual differences depending on the size of the individual, and the phase of the respiratory cycle (the intercostal spaces widen during normal inspiration).

Furthermore, there are substantial regional size differences, e.g., the intercostal spaces are deeper anteriorly than posteriorly, and deeper between the superior than the inferior ribs. The lateral part of the intercostal space is the widest zone of the intercostal space (i.e., at the anterior axillary line). In addition to the differences in size from one individual to the next, the composition of the chest wall itself can vary from person to person and also differs based on the gender of the patient. The male chest wall is composed of a greater percentage of muscle tissue than the female chest wall. On the other hand, the female chest wall is composed of a greater percentage of adipose tissue than the male chest wall. Each intercostal space contains three muscles: the innermost intercostal muscles, the internal intercostal muscles, and the external intercostal muscles. In addition, each intercostal space contains a neurovascular bundle (intercostal vein, artery and nerve) that runs below the ribs. Further, the chest wall is covered superficially by muscles, connective tissue and skin. For example, the chest wall, in the fifth intercostal space, anterior axillary line is covered externally by the serratus anterior muscle. The chest wall thickness (CWT) is defined as the length from the thoracic epidermal surface to the parietal pleural lining of the lung. As with the intercostal spaces and chest wall composition, there can be a great variation in chest wall thickness from individual to individual and from location to location in the same individual. For example, studies have shown that the mean male CWT increases by 70% laterally, and by 30% posteriorly, as compared with the anterior chest wall. The mean female CWT increases by 86% laterally, and by 85% posteriorly, as compared with the anterior chest wall. Further, the position of the patient can also affect the CWT; the CWT is a few millimeters less when the patient is in a reclined position (torso 45 degrees from horizontal) as compared with the same measurement taken when the patient is in the supine position.

The above-described physical differences between individuals must be considered when inserting a chest tube into a patient. There are several other key factors that come into play when inserting chest tubes, including insertion location, penetration angle, and depth. The primary goals of the tube insertion are to effectively evacuate the unwanted air/blood from the pleural space while also avoiding or minimizing injury to the intercostal neurovascular bundle, lungs and other internal structures. In addition, the chest tube must be well secured to the chest wall so that it cannot be accidently dislodged, and it must also be easily removable once the pneumo/hemothorax is absorbed.

Several techniques are currently used to insert a chest tube, each of which involves a relatively lengthy manual procedure that requires knowledge and experience. The most common technique involves surgical preparation and draping at the site of the tube insertion (usually at the nipple level-fifth intercostal space, anterior to the midaxillary line on the affected side), administering of local anesthesia to the insertion site, and making a 2–3 cm horizontal incision. A clamp is inserted through the incision and spread until a tract large enough to accept a finger is created. Next, the parietal pleura is punctured with the tip of a clamp, and the physician places a gloved finger into the incision to clear adhesions and to confirm the presence of a free pleural space locally. The proximal end of the chest tube is clamped and the tube is advanced into the pleural space. As the chest tube is inserted, it is directed posteriorly and superiorly. In this position, the chest tube will effectively clear the pleural space of both air and blood.

Once the chest tube is appropriately in place (determined by listening to air movement using a stethoscope), the tube is connected to an underwater-seal apparatus or to another one-way valve in order to clear air/blood from the pleural space. The tube is sutured to the skin, dressing is applied, and the tube is taped to the chest.

Insertion of a chest tube using this standard technique can require more than 15 minutes to accomplish by a physician and requires extensive medical training to be performed properly. Further, while performing the procedure, the physician must attend to the patient receiving the chest tube and thus is precluded from attending to other patients.

Various other specialized techniques are known, including the use of a rigid trocar (a sharp-pointed instrument equipped with a cannula); "over-the-wire" techniques (involving the insertion of a needle, attached to a syringe, through an incision and into the pleural cavity, and the introduction of a guide wire used to guide the insertion of progressively larger dilators or angioplasty ballons, and finally a chest tube); peel-away introducers for the insertion of mini-thoracostomy tubes in patients with spontaneous pneumothorax; and disposable laparoscopic trocar-cannulae.

U.S. Pat. No. 5,478,329 to Temamian teaches a "Trocar-less Rotational Entry Cannula" which can be used for gaining access to the peritoneal cavity for insertion of a laproscope. The Temamian cannula has screw threads on its outer surface and has a lumen extending throughout the entire length of the cannula. In use, an incision is first made and the cannula is turned into the patient, leaving access to the body cavity from the outside via the lumen. Since the cannula has an opening large enough for a laproscope to be inserted into the peritoneal cavity, a cylindrical piece of tissue is removed from the patient during insertion. The cannula remains inserted in the patient in its entirety while in use.

Each of the above-mentioned specialized techniques, excluding the use of a trocar, may result in fewer complications than standard techniques. Most also require that an incision be made to initiate the insertion (since an incision reduces the "snugness" of the device with respect to the chest wall, an incision reduces the stability of the device which may cause the device to move, change the angle of penetration or result in an accidental disengagement of the device from the chest wall). However, all are lengthy and require an extensive training to perform. Such training is usually provided only to physicians. Since the Ternamian cannula remains inserted in the patient during use, its sharp tip in the vicinity of internal organs increases the possibility of injury resulting from its use. It would be desirable to have a method and apparatus for insertion of a chest tube which is simpler and can be performed more quickly and by medical support staff, rather than requiring the services of a highly trained physician or specialist.

SUMMARY OF THE INVENTION

The present invention is an improved device for gaining access to a body cavity for the purpose of inserting into the cavity a medical device, such as a chest tube. The device generally comprises a catheter and a cannula insertable into the catheter during an insertion procedure. The cannula has a cutting tip that extends beyond one end of the catheter. The cutting tip enables simple insertion of the device into the body without requiring substantial pushing force. Once the device is inserted in the body, the cannula is removed, leaving a path of entry into the body cavity, while removing the sharp cutting tip from the area to reduce the likelihood of injury to a patient in whom the device is inserted.

In a first embodiment, the present invention is a tube insertion device, comprising: a generally tubular catheter having a distal end and a proximal end; and a cannula having a cutting tip at a distal end, the cannula being insertable into the proximal end of the catheter during an insertion procedure so that the distal end of the cannula extends beyond the distal end of the catheter to provide the tube insertion device with a cutting tip. In a preferred embodiment, the cutting tip comprises a tapered, threaded section terminating in a point at the distal end of said cannula, and the catheter includes a threaded section along its outer diameter, so that when the cannula is inserted into the catheter, the threaded section of the catheter and the threaded section of the cutting tip coincide to form an essentially continuous threaded section along the tube insertion device.

DESCRIPTION OF THE PREFERRED EMBODIMENTS

Figures 1, 2, 3:
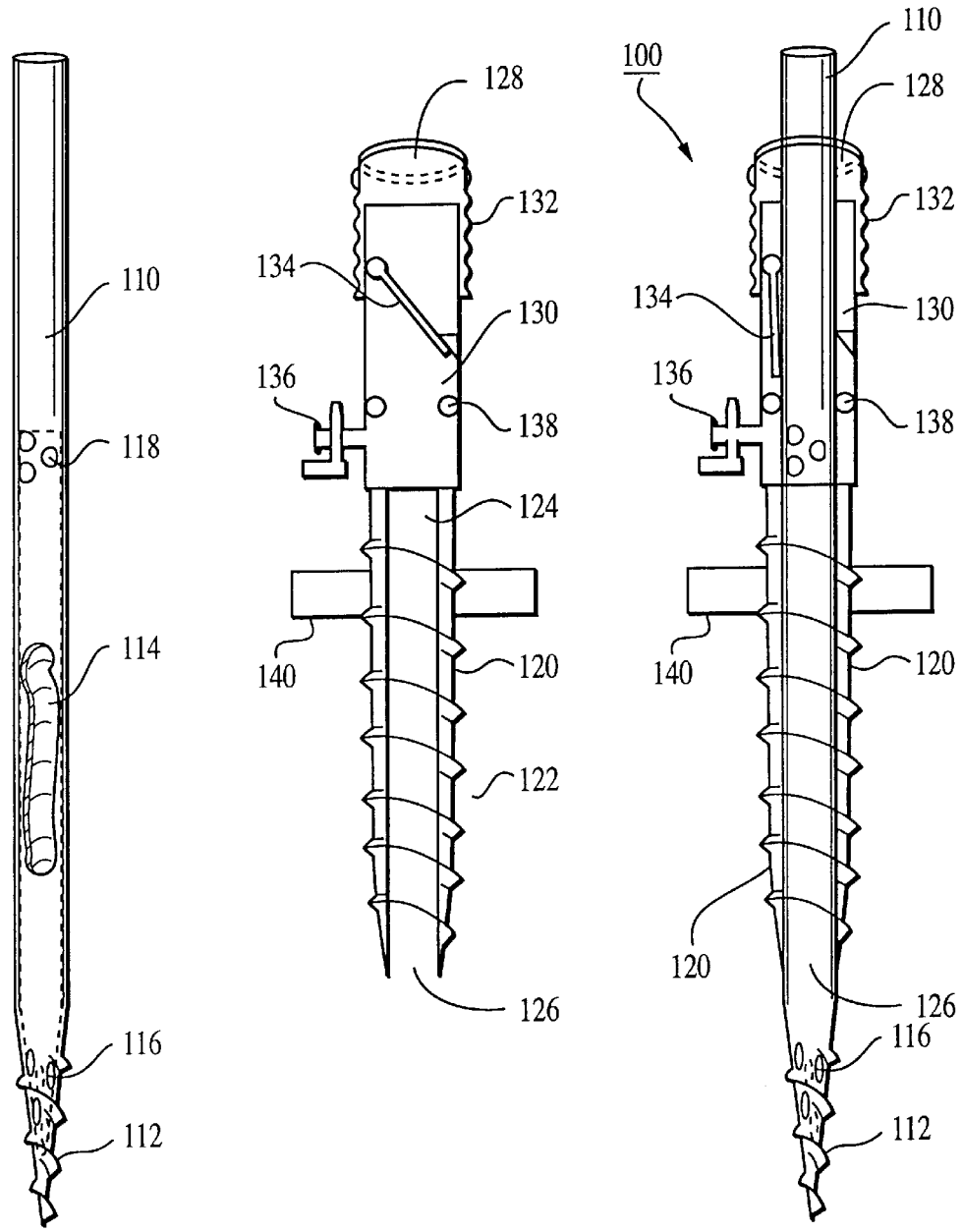
FIGS. 1–3 illustrate a first embodiment of a device constructed in accordance with the present invention.

FIGS. 1–3 illustrate a first embodiment of a device constructed in accordance with the present invention. A tube inserter 100 includes a cannula 110 having a threaded cutting portion 112 at its distal end and a conduit 114 (shown in dashed line in FIG. 1) running from its distal end along a portion of the length of the cannula 110. Holes 116 formed in the tip of cannula 110 and holes 118 formed in the side of cannula 110 create a fluid passageway from the holes 116 to the holes 118 along conduit 114.

A catheter 120 comprises an outer tube having an outer threaded portion 122 at the distal end and a lumen 124 running along its entire length, with the ends of the lumen 124 defining a distal opening 126 and a proximal opening 128. In a preferred embodiment the catheter 120 includes graduated markings (not shown) on the outer surface to indicate distances, for example, the distance from each graduation to the cutting tip 112. In addition, if desired, the graduated markings can be angled so that they provide the user of the device with an indication of the preferred insertion angle.

At the proximal end of catheter 120 is a head assembly 130, which includes a check valve 134, a port 136 and an O-ring 138. In the embodiment illustrated in FIGS. 1–3, a threaded outer portion 132 is shown, to provide a compression fit between a chest tube inserted in the catheter and the head assembly, as discussed in more detail below. A control device, such as a Leur cap, is affixed or otherwise associated with port 136 to enable control of the flow of fluid or other materials therethrough. The location of port 136 along the catheter 120 should coincide with the holes 118 when the cannula 110 is inserted into the catheter 120 as shown in FIG. 3. The O-ring (or other sealing means) is positioned within the lumen 124 such that, when the cannula 110 is inserted into the catheter 120 as shown in FIG. 3, it allows fluid to travel from the distal end of the tube inserter 100, through holes 116, through conduit 114, and out through holes 118 to port 136, while preventing the flow of fluid towards the portion of the proximal end of the tube inserter 100 past port 136.

An adjustable flange 140 is positionable along the threaded portion 122 of catheter 120. Its position can be adjusted to be closer to or farther from the distal end of the tube inserter 100. In a preferred embodiment the adjustable flange comprises a disk having a centrally-located opening formed therein, with the opening having internal threading to match the external threading of threaded portion 122. So configured, the adjustable flange can be moved up or down the catheter 120 by rotation of the adjustable flange thereon. Although not shown, if desired the adjustable flange 140 can be angled to the preferred insertion angle to act as a guide for the user.

Check valve 134 allows the cannula 110 to be inserted into the lumen 124 when desired (shown inserted in FIG. 3). When cannula 110 is removed from lumen 124 (shown in FIG. 2), the check valve 134 prevents the inflow or out flow of fluids (or any material or composition) through the proximal opening 128.

Figure 4:
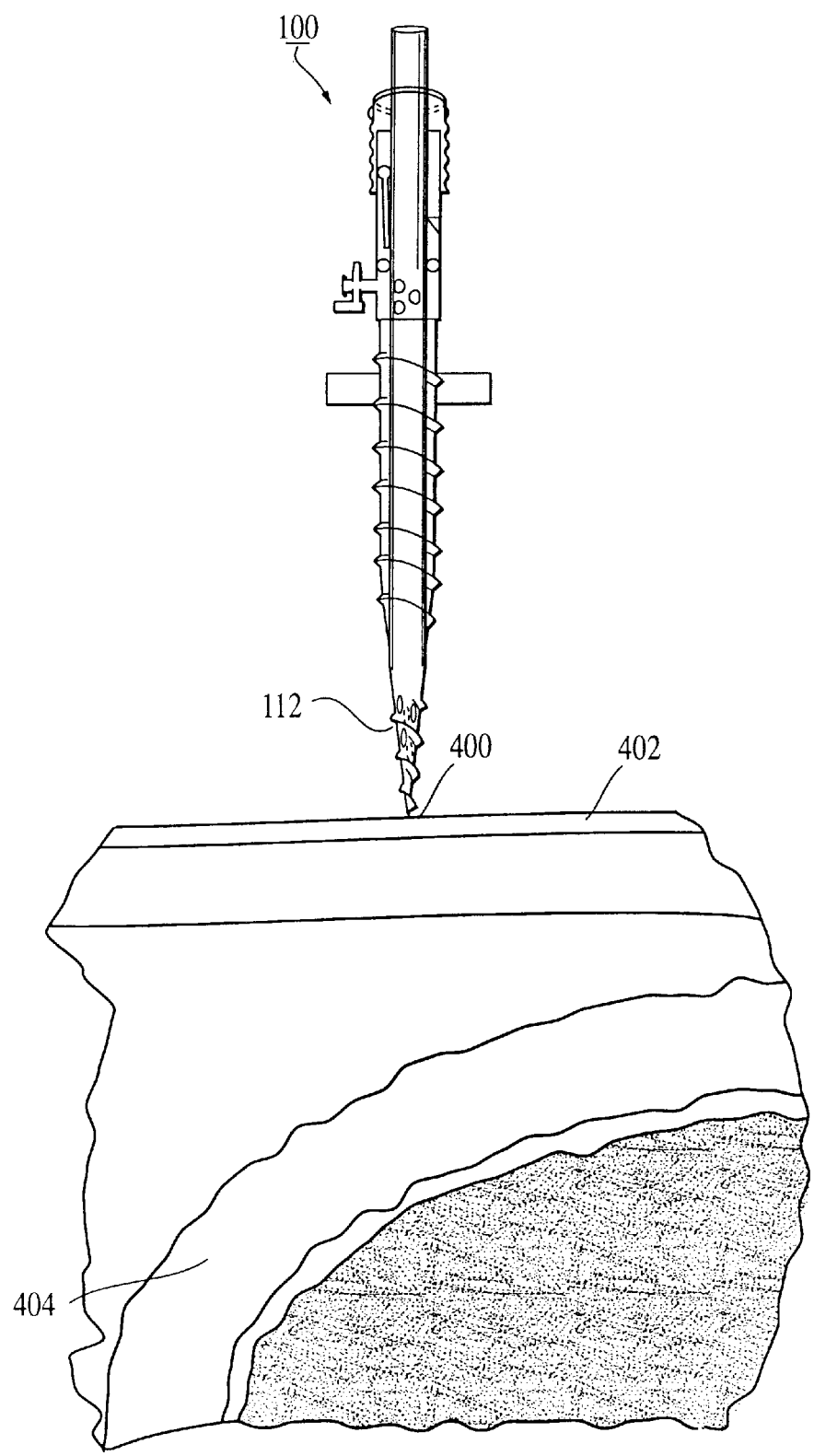
FIGS. 4–7 illustrate a method of using the device of FIGS. 1–3 for insertion of a chest tube.

Referring to FIGS. 4–7, the method of using the present invention for insertion of a chest tube is now described. Referring to FIG. 4, the tube inserter 100, fully assembled as shown in FIG. 3, is placed tip first against the insertion location 400 on the skin 402 of a patient so that the threaded cutting portion 112 is in contact with the entrance location. The entire tube inserter 100 is then turned and advanced into the pleural space 404. The screw design allows for a controlled insertion into the chest, with minimal pushing force, since progression relies on rotation of the pitched screw threads. The threaded cutting portion 112 eliminates the need for an initial incision, and the air/fluid passageway in the cannula 110 provides a method for the user of the device to determine whether the tip of the device is in the pleural space 404 and the nature of the injury (e.g., the presence of blood at port 136 indicates the presence of hemothorax).

Figure 5:
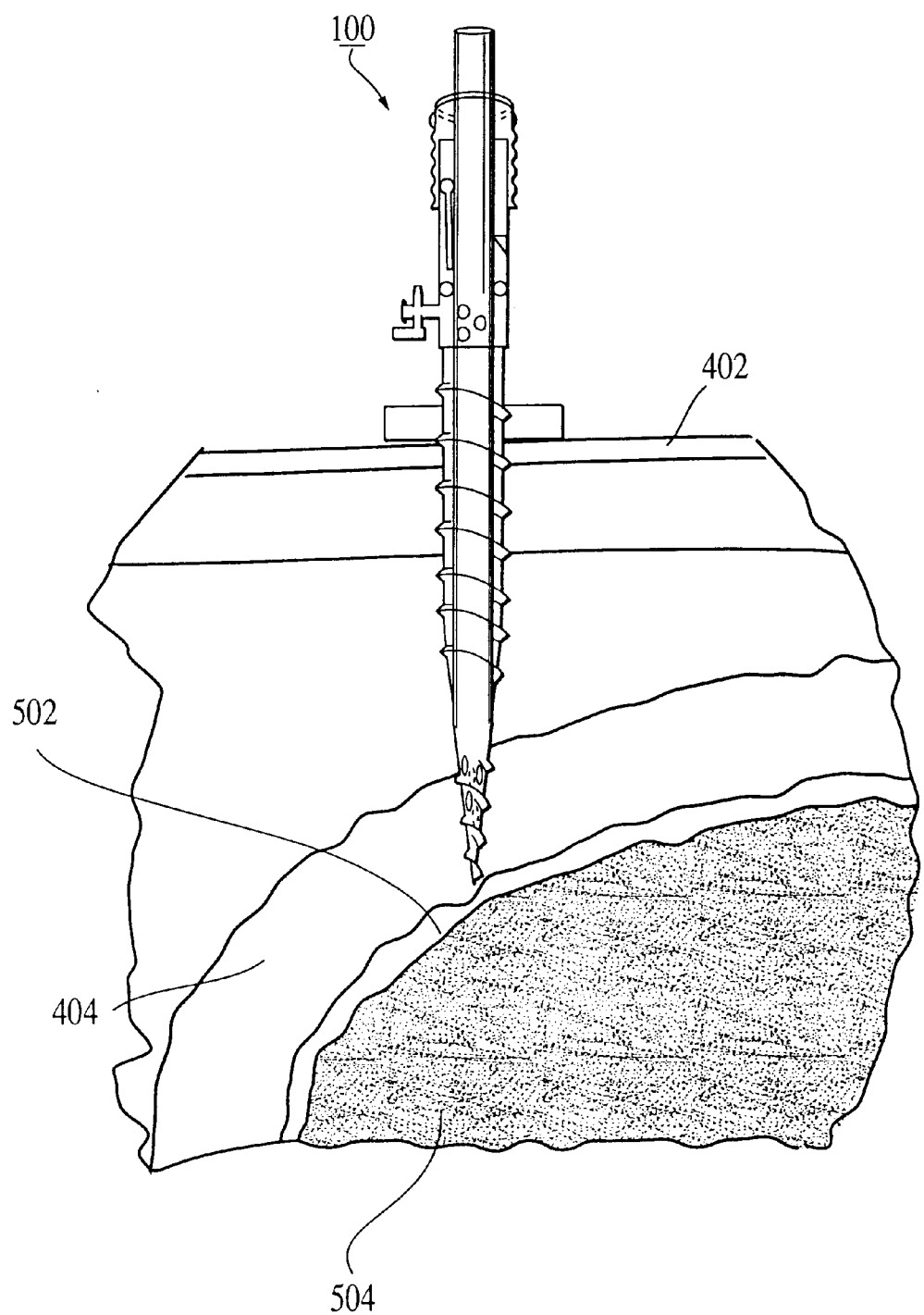

As shown in FIG. 5, the adjustable flange 140 limits the depth of the penetration by stopping the insertion at the skin 402, and therefore minimizes the risk of injury to internal organs, such as to lung 504. Further, the ability to easily adjust the depth of penetration using adjustable flange 140 allows a non-physician to simply set the depth and be assured that a maximum depth is not exceeded. FIG. 5 illustrates the tube inserter 100 fully inserted into the patient, such that the threaded cutting portion 112 has pierced the parietal pleura and entered the pleural space 404. Note that the cutting portion 112 has stopped short of contacting the visceral pleura 502 and the lung 504.

Figure 6:
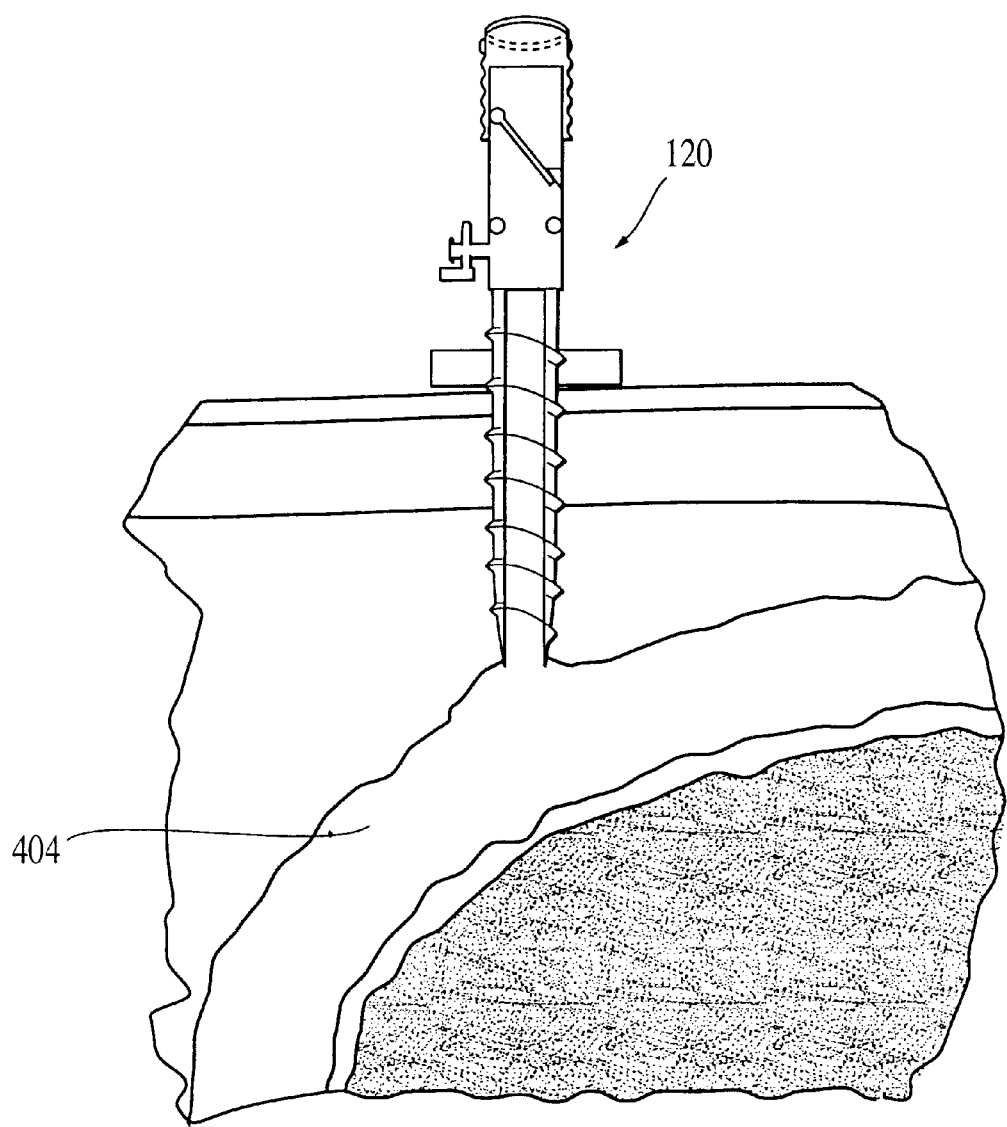
Figure 7:
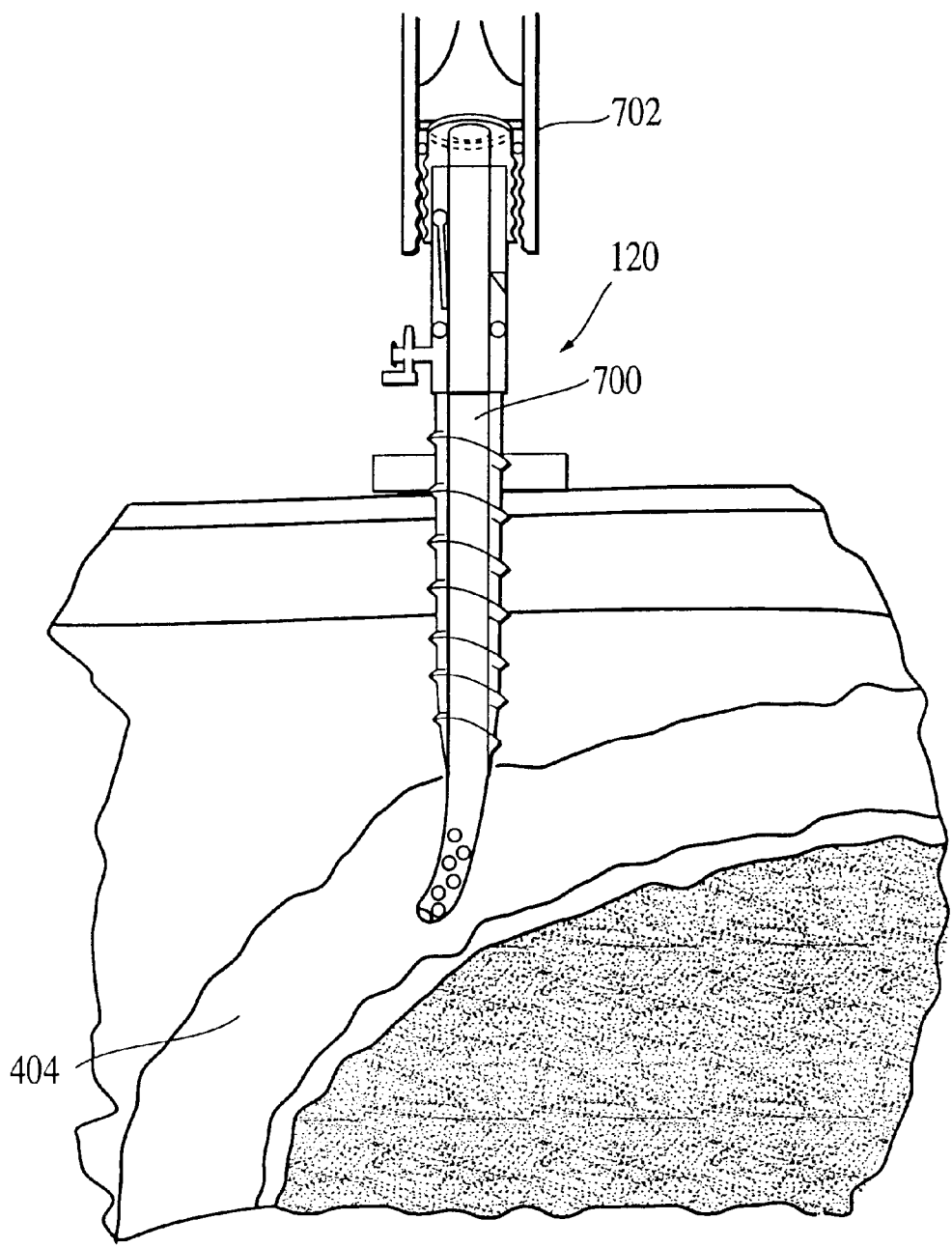

When insertion is complete and it has been determined that the device tip is in the pleural space 404, as shown in FIG. 6, the cannula 110 along with its threaded cutting portion 112 is removed, leaving the catheter 120 in place, with the check valve and Leur cap closed. A chest tube 700, which is connected to a Heimlich valve or other type of one-way valve, can now be advanced into the pleural space 404 as shown in FIG. 7. Preferably the chest tube 700 is locked or otherwise secured in place in the catheter 120 during use, to prevent it from accidentally being advanced into or retracted from the pleural cavity. For example, the chest tube 700 can be supplied with a mating device 702 having an internal threading which matches the outer threading 132 of catheter 120; the exact method and structure for maintaining the chest tube in place is not the focus of this invention and therefore any method and structure for maintaining a tight or "compression fit" is contemplated by the previous description. The excavation of pneumothorax and/or hemothorax is carried out in the usual manner using the chest tube and the appropriate removal methods and apparatus.

The device can be inserted to the chest wall at various angles with minimal normal ("push") and rotational forces, and with a high degree of control of insertion depth. While in this operative position, the chest tube and catheter 120 remain positionally stable within the chest wall. Due to the threading along the outer surface of the catheter 120, a high degree of force is required to pull the assembly out accidentally. Further, once the pneumothorax or hemothorax has been resolved, the apparatus is easily removed from the chest by rotating the apparatus out along the threads.

Figure 8:
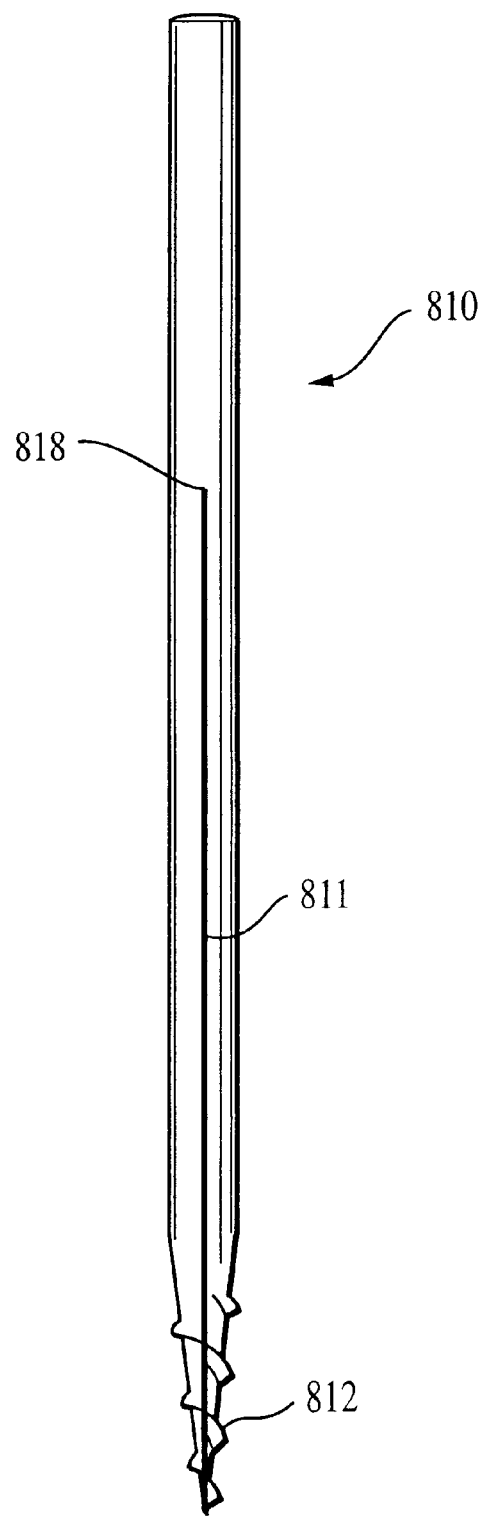
FIG. 8 illustrates an alternative embodiment of a cannula in accordance with the present invention.

FIG. 8 illustrates an alternative embodiment for the cannula of the present invention. As shown in FIG. 8, a cannula 810 has a spline 811 running from the cutting tip 812 up to a location 818. Location 818 is selected so that it will be adjacent to port 136 (FIG. 2) when the cannula is inserted into catheter 120. The spline provides a fluid passage (i.e., a conduit) along the outer edge of the cannula (between the cannula 110 and the inner wall of catheter 120) so that fluid may pass from the tip of the cannula to the port 136, as described above with respect to FIGS. 1–3.

While there are many materials that can be used to fabricate the device of the present invention, in a preferred embodiment the cutting tip 112 is made of stainless steel or titanium in a generally conical shape, with threads, and converging at a sharpened tip at the distal end thereof. The remainder of the device, in a preferred embodiment, is made of injection molded clear plastic so that fluid traveling through the device may be viewed by the user. Obviously other materials can be used without detracting from the novel aspects of the invention disclosed herein.

The present invention enables prompt and inexpensive management of pneumo/hemothorax in humans and has broad-range application in areas such as combat casualty care, fire and rescue, and shock trauma centers. Further, while the present invention is disclosed and described in a preferred embodiment pertaining to chest tubes, it is understood and contemplated that it can be applied to insertion devices of other types, such as abdominal drains and drains inserted into joints or other body cavities; introduction of a port of entry into the body (e.g., pleural and peritoneal spaces, joints) for diagnostic and therapeutic purposes; introduction of a laproscope, and firm and stable fixation of other medical instrumentation to soft tissues (e.g., chest and abdominal wall) using the screw concept disclosed herein.

The foregoing is considered as illustrative only of the principles of the invention. Further, since numerous modifications and changes will readily occur to those skilled in the art, it is not desired to limit the invention to the exact construction and applications shown and described. Accordingly, all suitable modifications and equivalents may be resorted to, falling within the scope of the invention and the appended claims and their equivalents.

What is claimed is:

1. A tube insertion device, comprising: a generally tubular catheter having a distal end and a proximal end; and a cannula having a cutting tip at a distal end, said cannula insertable into said proximal end of said catheter during an insertion procedure so that said distal end of said cannula extends beyond the distal end of said catheter to provide said tube insertion device with a cutting tip;

wherein said cutting tip comprises a tapered, threaded section terminating in a point at the distal end of said cannula;

wherein said catheter including a threaded section along its outer diameter, so that when said cannula is inserted into said catheter, the threaded section of said catheter and the threaded section of said cutting tip coincide to form an essentially continuous threaded section along the tube insertion device;

wherein said catheter includes a head assembly at said proximal end, said head assembly including a port located between said distal and proximal ends of said catheter, and wherein said cannula includes a conduit running from said cutting tip to a location adjacent said port when said cannula is inserted into said catheter, thereby creating a passage between said cutting tip and said port.

2. A tube insertion device as set forth in claim 1, wherein said conduit comprises a hollowed-out portion extending from the distal end of said cannula to said location adjacent said port, and openings formed in said cannula at either end of said hollowed-out portion, thereby forming a fluid passageway between said cutting tip and said port through said conduit when said cannula is inserted in said catheter.

3. A tube insertion device as set forth in claim 2, wherein said catheter further includes an adjustable depth-limiter which can be adjusted to limit the depth of insertion of said tube insertion device.

4. A tube insertion device as set forth in claim 3, wherein said head assembly includes a check valve inside said catheter, said check valve being in an open position when said cannula is inserted in said catheter and in a closed position when said cannula is removed from said catheter.

5. A tube insertion device as set forth in claim 4, wherein said head assembly includes means for connecting a chest tube thereto, and wherein a chest tube is connectable to said catheter so that a distal end of said chest tube extends into said catheter, opens said check valve, and extends out through the distal opening.

6. A tube insertion device as set forth in claim 1, wherein said conduit comprises at least one spline extending from the distal end of said cannula to said location adjacent said port, thereby forming a fluid passageway between said cutting tip and said port through said conduit when said cannula is inserted in said catheter.

7. A method for accessing a body cavity of a patient comprising the steps of:

providing a tube insertion device having a generally tubular catheter having a distal end and a proximal end;

providing a cannula having a cutting tip at a distal end;

inserting said cannula being insertable into said proximal end of said catheter so that said distal end of said cannula extends beyond the distal end of said catheter to provide said tube insertion device with a cutting tip;

placing said cutting tip against the skin of said patient at an insertion location;

turning said tube insertion device to advance said tube insertion device into the patient a predetermined distance; and removing said cannula thereby creating an access to the body cavity through said catheter.

* * * * *